United States Patent
Lygin et al.

(10) Patent No.: US 10,934,245 B2
(45) Date of Patent: Mar. 2, 2021

(54) METHOD FOR PRODUCING A HOMOGENEOUS CATALYST FOR THE TISHCHENKO REACTION

(71) Applicant: EVONIK OPERATIONS GMBH, Essen (DE)

(72) Inventors: Alexander Lygin, Griesheim (DE); Steffen Krill, Mühltal (DE); Matthias Grömping, Darmstadt (DE); Andreas Tepperis, Bad König (DE)

(73) Assignee: EVONIK OPERATIONS GMBH, Essen (DE)

( * ) Notice: Subject to any disclaimer, the term of this patent is extended or adjusted under 35 U.S.C. 154(b) by 0 days.

(21) Appl. No.: 16/614,332

(22) PCT Filed: May 14, 2018

(86) PCT No.: PCT/EP2018/062298
§ 371 (c)(1),
(2) Date: Nov. 15, 2019

(87) PCT Pub. No.: WO2018/210706
PCT Pub. Date: Nov. 22, 2018

(65) Prior Publication Data
US 2020/0148621 A1 May 14, 2020

(30) Foreign Application Priority Data
May 17, 2017 (DE) .......................... 10 2017 208 303

(51) Int. Cl.
*C07C 67/44* (2006.01)
*B01J 31/14* (2006.01)
*C07C 69/54* (2006.01)

(52) U.S. Cl.
CPC ............ *C07C 67/44* (2013.01); *B01J 31/143* (2013.01); *C07C 69/54* (2013.01)

(58) Field of Classification Search
CPC ......... C07C 67/44; C07C 69/54; B01J 31/143
See application file for complete search history.

(56) References Cited

U.S. PATENT DOCUMENTS 1,785,166 A * 12/1930 Young .................... C07C 69/14
                                                           560/238
2,250,520 A    7/1941  Bludworth
2,516,627 A    7/1950  Hearne et al.
2018/0334423 A1  11/2018  Lygin et al.

FOREIGN PATENT DOCUMENTS

JP         H05-43514       2/1993

OTHER PUBLICATIONS

Robert Baker, J.A.C.S., (1938), 60(11), p. 2673-2675.*
English language translation of the International Search Report for corresponding PCT/EP2018/062298, filed May 14, 2018.
English language translation of the Written Opinion of the International Searching Authority for corresponding PCT/EP2018/062298, filed May 14, 2018.
English language translation of the International Preliminary Report on Patentability for PCT/EP2018/062298, filed May 14, 2018.
Helvetica Chimica Acta, "266. Zur Disproportionierung aliphatischer Aldehyde. III Über die Reaktion von Tischtschenko," *Neuchhtel Am. SOC J. Org. Chem.*:2172-2181 (Jan. 1951); with English language machine translation of p. 1 of document.
Mehrota, "Aluminium Amyloxides," *Jour. Indian Chem. Soc. 31*(2):85-90 (Dec. 1954).
Terelak, et al., "Process for production of butyl butyrate from butyraldehyde," *Przemysl Chemiczny 83*(7): Abstract only (Dec. 2004).
U.S. Appl. No. 15/967,463, filed Apr. 30, 2018, US 2018-0334423 A1, Nov. 22, 2018, Lygin.
Terelak, et al., "Process for production of butyl butyrate from butyraldehyde," *Przemysl Chemiczny 83*(7):331-334 (Dec. 2004).

* cited by examiner

*Primary Examiner* — Yong L Chu
(74) *Attorney, Agent, or Firm* — Law Office of Michael A. Sanzo, LLC

(57) ABSTRACT

The invention relates to a process for preparing a carboxylic ester by reacting an aldehyde in the presence of an aluminum alkoxide, wherein the aluminum alkoxide is obtained either by reacting an aluminum hydride with an aldehyde or by reacting a different aluminum alkoxide with a carboxylic ester.

14 Claims, No Drawings

METHOD FOR PRODUCING A HOMOGENEOUS CATALYST FOR THE TISHCHENKO REACTION

CROSS REFERENCE TO RELATED APPLICATIONS

The present application is US national stage of international application PCT/EP2018/062298, which had an international filing date of May 14, 2018, and was published on Nov. 22, 2018. The application claims priority to DE 10 2017 208 303.4, filed on May 17, 2017.

The invention relates to a process for preparing aluminum alkoxides and the use thereof as homogeneous catalysts for the Tishchenko reaction.

Carboxylic esters are typically prepared by the acid-catalyzed reaction of alcohols with carboxylic acids (esterification) or by reaction of alcohols with other carboxylic esters (transesterification). In the case that certain alcohols are not readily obtainable or are expensive, which applies to methallyl alcohol for example, it is more favorable to start from other more readily obtainable raw materials, for example aldehydes. Furthermore, it is particularly advantageous if only one reactant rather than two has to be used for preparing the carboxylic esters.

These advantages are realized by the catalytic conversion of aldehydes to carboxylic esters. This reaction is also known in the prior art as the Tishchenko reaction or Claisen-Tishchenko reaction. In this context, two aldehydes react by rearrangement in the presence of an aluminum alkoxide to give a carboxylic ester, in accordance with the following reaction scheme (here using the example of aluminum triethoxide as catalyst):

U.S. Pat. No. 2,516,627 describes the preparation of allyl acrylate by reacting acrolein in the presence of aluminum triisopropoxide (Al(OiPr)$_3$) in benzene as solvent. Al(OiPr)$_3$ is present in this case as a soluble homogeneous catalyst. Al(OiPr)$_3$ is prepared separately by reacting aluminum with isopropanol using a catalyst, such as mercury chloride for example. The maximum yield of allyl acrylate in this method is 40%, and considerable amounts of allyl alcohol are isolated as by-product.

U.S. Pat. No. 2,250,520 describes the preparation of methallyl methacrylate from methacrolein in the presence of aluminum trimethallylalkoxide (Al(OMethallyl)$_3$) in benzene as solvent. The aluminum alkoxide is again present as a homogeneous catalyst. The catalyst is prepared in a separate reaction of aluminum with methallyl alcohol using mercury chloride and iodine.

JP 05043514 A describes the preparation of methallyl methacrylate from methacrolein in the presence of an aluminum alkoxide, for example aluminum tri-n-butoxide. In this case, however, mixed esters are formed as by-product, i.e. carboxylic esters with n-butyl radical, which can only be separated with difficulty from the methallyl methacrylate.

A disadvantage of the process described is the fact that the homogeneous aluminum alkoxide catalyst has to be prepared in a separate reaction using toxic additives such as mercury chloride.

In light of this background, it is an object of the present invention to provide a simplified process for preparing aluminum alkoxides for the Tishchenko reaction, which process dispenses with toxic additives. Moreover, the process according to the invention is to allow the in situ preparation of the catalyst in the reaction medium of the Tishchenko reaction.

This object is achieved by a process for preparing a carboxylic ester, comprising the following steps:
a) preparing an aluminum alkoxide of the general formula (I)

$$Al(OCH_2R^1)_3 \qquad (I)$$

by reacting an aldehyde of the general formula (II)

$$R^1CHO \qquad (II)$$

with an aluminum hydride;
and
b) reacting an aldehyde of the general formula (II) in the presence of the aluminum alkoxide of the general formula (I) to give a carboxylic ester of the general formula (III)

$$R^1-CO-OCH_2-R^1 \qquad (III);$$

where $R^1$ is an alkyl, alkenyl or alkynyl group.

The process according to the invention makes it possible to prepare the catalyst required for the Tishchenko reaction by reaction with the reactant of the Tishchenko reaction, the aldehyde, in a simple manner. This does not require any further additives or catalysts, such as mercury chloride, for example. In this way, the catalyst required for the Tishchenko reaction is prepared in situ in the reaction medium of the Tishchenko reaction and can be used directly for converting the aldehyde to a carboxylic ester. No elaborate purification or isolation of the aluminum alkoxide needs to be performed in this case. Nor do undesirable additives need to be removed from the reaction medium before the conversion to the carboxylic ester.

The temperature during the reaction of the aldehyde with the aluminum hydride is selected such that selective formation of the catalyst is ensured. In one embodiment, the reaction of the aldehyde with the aluminum hydride to give the aluminum alkoxide takes place at a temperature of 70° C. down to −30° C., preferably at a temperature of 50° C. down to −25° C., particularly preferably at a temperature of 30° C. down to −20° C., most particularly preferably at a temperature of 20 down to −15° C., in order to ensure selective formation of the catalyst.

Since the reaction of the aldehyde with the aluminum hydride generally proceeds exothermically, the reaction mixture is preferably cooled during the reaction of the aldehyde with the aluminum hydride.

The reaction temperature during the reaction of the aldehyde with the aluminum hydride is preferably selected such that the aldehyde is in liquid form. Accordingly, in one embodiment, a temperature above the melting point of the aldehyde is selected.

After a sufficient amount of aluminum alkoxide has formed, the remaining aldehyde can be reacted in the presence of the aluminum alkoxide to give the carboxylic ester. This is preferably accomplished by increasing the temperature. In one preferred embodiment, the reaction of the aldehyde to give the carboxylic ester therefore takes place at a temperature of at least 0° C., preferably at least 10° C., particularly preferably at least 20° C.

The reaction temperature during the reaction of the aldehyde to give the carboxylic ester is preferably below the boiling point of the aldehyde and of the carboxylic ester.

In one embodiment, the reaction of the aldehyde to give the carboxylic ester takes place at a temperature of 0 to 100° C., preferably 10 to 80° C., particularly preferably 15 to 50° C., most preferably 20 to 30° C.

The $R^1$ radical of the aldehyde used determines the structure of the aluminum alkoxide formed and of the carboxylic ester formed. By virtue of the fact that the $R^1$ radicals are identical in the aluminum alkoxide prepared according to the invention and in the aldehyde used, there is no formation of undesirable mixed esters, but exclusively formation of the desired carboxylic ester of the general formula (III).

In one preferred embodiment, $R^1$ is a —$(C_1$-$C_{12})$-alkyl group or a —$(C_2$-$C_{12})$-alkenyl group and may optionally be substituted by one or more substituents selected from —$(C_1$-$C_{12})$-alkyl, —$(C_3$-$C_{12})$-cycloalkyl, —$(C_4$-$C_{12})$-heterocycloalkyl, —$(C_6$-$C_{20})$-aryl, —$(C_4$-$C_{20})$-heteroaryl, —O—$(C_1$-$C_{12})$-alkyl, —O—$(C_3$-$C_{12})$-cycloalkyl, —S—$(C_1$-$C_{12})$-alkyl, —S—$(C_3$-$C_{12})$-cycloalkyl, —COO—$(C_1$-$C_{12})$-alkyl, —COO—$(C_3$-$C_{12})$-cycloalkyl, —CONH—$(C_1$-$C_{12})$-alkyl, —CONH—$(C_3$-$C_{12})$-cycloalkyl, —N—[$(C_1$-$C_{12})$-alkyl]$_2$, —OH, —$NH_2$, halogen.

Particularly preferred substituents are —$(C_1$-$C_{12})$-alkyl, —$(C_3$-$C_{12})$-cycloalkyl, —$(C_6$-$C_{20})$-aryl.

In the context of the invention, the following definitions of terms apply.

$(C_1$-$C_{12})$-alkyl groups are linear or branched alkyl groups having 1 to 12 carbon atoms. Suitable $(C_1$-$C_{12})$-alkyl groups are especially methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,1,2-trimethylpropyl, 1,2,2-trimethylpropyl, 1-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

$(C_2$-$C_{12})$-alkenyl groups are linear or branched alkenyl groups having 2 to 12 carbon atoms and one or more C—C double bonds. Suitable $(C_2$-$C_{12})$-alkenyl groups are especially vinyl (ethenyl), allyl (propenyl) and methallyl (isobutenyl).

$(C_3$-$C_{12})$-cycloalkyl groups are cycloalkyl groups having 3 to 12 carbon atoms. Suitable $(C_3$-$C_{12})$-cycloalkyl groups are especially cyclopropyl, cyclobutyl, cyclopentyl, cyclohexyl, cycloheptyl, cyclooctyl, cyclododecyl, cyclopentadecyl, norbornyl, adamantyl.

$(C_4$-$C_{12})$-heterocycloalkyl groups are cycloalkyl groups having 4 to 12 carbon atoms and any number of heteroatoms. Preferred heteroatoms are O, N and S. Suitable $(C_4$-$C_{12})$-heterocycloalkyl groups are especially tetrahydrothiophenyl, tetrahydrofuryl, tetrahydropyranyl and dioxanyl.

$(C_6$-$C_{20})$-aryl groups are aromatic hydrocarbon groups having 6 to 20 carbon atoms. Suitable $(C_6$-$C_{20})$-aryl groups are especially phenyl, naphthyl, indenyl, fluorenyl, anthracenyl, phenanthrenyl, naphthacenyl, chrysenyl, pyrenyl, coronenyl. Preferred $(C_6$-$C_{20})$-aryl groups are phenyl, naphthyl and anthracenyl.

$(C_4$-$C_{20})$-heteroaryl groups are aromatic hydrocarbon groups having 4 to 20 carbon atoms and any number of heteroatoms. Preferred heteroatoms are O, N and S. Suitable $(C_4$-$C_{20})$-heteroaryl groups are especially furyl, thienyl, pyrrolyl, oxazolyl, isoxazolyl, thiazolyl, isothiazolyl, imidazolyl, pyrazolyl, furazanyl, tetrazolyl, pyridyl, pyridazinyl, pyrimidyl, pyrazinyl, benzofuranyl, indolyl, isoindolyl, benzimidazolyl, quinolyl, isoquinolyl.

Preferred halogen substituents are F, Cl and Br.

The $R^1$ radical is preferably a —$(C_2$-$C_{12})$-alkenyl group which is optionally substituted as described above. $R^1$ is particularly preferably an unsubstituted —$(C_2$-$C_{12})$-alkenyl group. $R^1$ is most preferably ethenyl or 2-propenyl. The preferred aldehyde used is accordingly acrolein or methacrolein.

The aluminum hydride to be used according to the invention is a compound containing at least one Al—H group.

The aluminum hydride is preferably used in deficiency in relation to the aldehyde, so that the aluminum hydride can be completely reacted to give the aluminum alkoxide and a residual amount of aldehyde remains, which can be reacted to give the carboxylic ester in the following step. The amount of aluminum hydride is in this case preferably selected such that the molar amount of Al, based on the molar amount of the aldehyde, is 0.1 to 10 mol %, preferably 0.2 to 5 mol %, particularly preferably 0.5 to 3 mol %.

Preferably used as aluminum hydride are compounds having the empirical formula $AlH_3$ (corresponding to compounds having the empirical formula $(AlH_3)_x$, where x=1 or x>1), also referred to as alanes, or complex metal aluminum hydrides. The term "complex metal aluminum hydride" is understood within the meaning of this invention in particular to be compounds of the empirical formula $M(AlH_4)_n$ and $M'_3(AlH_6)$, where M may be for example Li, Na, K, Mg, Ca, Ba, Sn(II) and Ti(IV), n takes values of 1, 2 or 4 depending on M, and M' is for example Li or Na. Suitable complex metal aluminum hydrides are for example $LiAlH_4$, $NaAlH_4$, $KAlH_4$, $Mg(AlH_4)_2$, $Ca(AlH_4)_2$, $Ba(AlH_4)_2$, $Sn(II)(AlH_4)_2$, $Ti(IV)(AlH_4)_4$.

In one embodiment, the aluminum hydride is selected from $LiAlH_4$, $NaAlH_4$, $KAlH_4$, $Mg(AlH_4)_2$, $Ca(AlH_4)_2$, $Ba(AlH_4)_2$, $Sn(II)(AlH_4)_2$, $Ti(IV)(AlH_4)_4$, and mixtures thereof. Preferably used are $LiAlH_4$, $NaAlH_4$, $KAlH_4$, $Mg(AlH_4)_2$, $Ca(AlH_4)_2$, $Ba(AlH_4)_2$. Particularly preferably used are $LiAlH_4$, $NaAlH_4$, $KAlH_4$. Most preferably used is $LiAlH_4$.

If a complex metal aluminum hydride is used as starting material, the corresponding tetraalkoxyaluminate is generally initially formed in the reaction with the aldehyde. In order to convert the tetraalkoxyaluminate to the desired aluminum alkoxide of the formula $Al(OR^1)_3$, an acid may be added to the reaction mixture in step a). The addition of the acid preferably takes place after the addition of the metal aluminum hydride. Aluminum halides or other Lewis acids, for example $ZnCl_2$, $BCl_3$ etc., and also HCl, $H_2SO_4$, $HNO_3$, $H_3PO_4$ or other mineral acids may be used as acid, for example. Preferably, at least one aluminum salt is used as acid. By way of example, aluminum halides such as $AlF_3$, $AlCl_3$, $AlBr_3$ or $AlI_3$ may be used here. Preferably, use is made of $AlCl_3$.

In one embodiment, the process in step a) comprises reacting an aldehyde of the general formula $R^1CHO$ with a complex metal aluminum hydride and subsequently reacting the resulting product with an aluminum salt, in particular an aluminum halide, to give an aluminum alkoxide of the general formula $Al(OCH_2R^1)_3$.

In one preferred embodiment, the aldehyde of formula (I) is acrolein or methacrolein and the aluminum hydride is $LiAlH_4$, $NaAlH_4$ or $KAlH_4$. Preferably, in this embodiment, the product resulting from the reaction of aldehyde and aluminum hydride is reacted with an aluminum halide, in particular $AlCl_3$, to give the aluminum alkoxide of the general formula $Al(OCH_2R^1)_3$.

The process according to the invention can be carried out with or without addition of a solvent. Preferably, no solvent is used.

If a solvent is used, consideration can be given here for example to hydrocarbons such as n-pentane, n-hexane, cyclohexane, heptane, octane, decane etc., aromatic compounds such as benzene, toluene, xylene etc., esters such as ethyl acetate, ethers such as diethyl ether, methyl tert-butyl ether etc.

In a second variant, the present invention relates to a process for preparing a carboxylic ester, comprising the following steps:

a) preparing an aluminum alkoxide of the general formula (I)

$$Al(OCH_2R^1)_3 \quad (I)$$

by reacting an aluminum alkoxide of the general formula (Ia)

$$Al(OCH_2R^2)_3 \quad (Ia)$$

with a carboxylic ester of the general formula (IIIa)

$$R^3\text{—CO—OCH}_2\text{—}R^1 \quad (IIIa);$$

and b) reacting an aldehyde of the general formula (II)

$$R^1CHO \quad (II)$$

in the presence of the aluminum alkoxide of the general formula (I) to give a carboxylic ester of the general formula (III)

$$R^1\text{—CO—OCH}_2\text{—}R^1 \quad (III);$$

where $R^1$, $R^2$, $R^3$ are in each case alkyl, alkenyl or alkynyl groups and $R^1$ and $R^2$ are different organic groups.

In this variant, the catalyst is obtained by ligand exchange reaction between an aluminum alkoxide of the formula (Ia) and a carboxylic ester of the formula (IIIa). The reaction product of the Tishchenko reaction, the carboxylic ester of the formula (III), may also be used in this case as carboxylic ester of the formula (IIIa). Therefore, this variant makes possible the preparation of the catalyst in the reaction medium of the Tishchenko reaction and hence the in situ preparation of the catalyst.

In one preferred embodiment, the ester of the formula (III) is used as carboxylic ester of the formula (IIIa). In this case, $R^1$ and $R^3$ are identical.

The $R^1$, $R^2$, $R^3$ radicals are in each case preferably a —$(C_1\text{-}C_{12})$-alkyl group or a —$(C_2\text{-}C_{12})$-alkenyl group and may optionally be substituted by one or more substituents selected from —$(C_1\text{-}C_{12})$-alkyl, —$(C_3\text{-}C_{12})$-cycloalkyl, —$(C_4\text{-}C_{12})$-heterocycloalkyl, —$(C_6\text{-}C_{20})$-aryl, —$(C_4\text{-}C_{20})$-heteroaryl, —O—$(C_1\text{-}C_{12})$-alkyl, —O—$(C_3\text{-}C_{12})$-cycloalkyl, —S—$(C_1\text{-}C_{12})$-alkyl, —S—$(C_3\text{-}C_{12})$-cycloalkyl, —COO—$(C_1\text{-}C_{12})$-alkyl, —COO—$(C_3\text{-}C_{12})$-cycloalkyl, —CONH—$(C_1\text{-}C_{12})$-alkyl, —CONH—$(C_3\text{-}C_{12})$-cycloalkyl, —N—$[(C_1\text{-}C_{12})\text{-alkyl}]_2$, —OH, —$NH_2$, halogen. In this case, $R^1$ and $R^2$ are different groups.

In one preferred embodiment, $R^1$ is a —$(C_2\text{-}C_{12})$-alkenyl group which is optionally substituted as described above. $R^1$ is particularly preferably an unsubstituted —$(C_2\text{-}C_{12})$-alkenyl group. $R^1$ is most preferably ethenyl or 2-propenyl.

In one preferred embodiment, $R^2$ is a —$(C_2\text{-}C_{12})$-alkyl group which is optionally substituted as described above. $R^2$ is particularly preferably an unsubstituted —$(C_2\text{-}C_{12})$-alkyl group. $R^2$ is most preferably selected from methyl, ethyl, n-propyl, isopropyl, n-butyl, isobutyl, sec-butyl, tert-butyl, n-pentyl, sec-pentyl, 3-pentyl, 2-methylbutyl, 3-methylbutyl, 3-methylbut-2-yl, 2-methylbut-2-yl, neopentyl.

In one preferred embodiment, $R^3$ is a —$(C_2\text{-}C_{12})$-alkenyl group which is optionally substituted as described above. $R^3$ is particularly preferably an unsubstituted —$(C_2\text{-}C_{12})$-alkenyl group. $R^3$ is most preferably ethenyl or 2-propenyl. Particularly preferably, $R^1$ and $R^3$ are identical.

In one preferred embodiment, $R^1$ and $R^3$ are in each case —$(C_2\text{-}C_{12})$-alkenyl groups, in particular ethenyl or 2-propenyl, and each $R^2$ radical is selected from methyl, ethyl, n-propyl, isopropyl, n-butyl, isobutyl, sec-butyl, tert-butyl, n-pentyl, sec-pentyl, 3-pentyl, 2-methylbutyl, 3-methylbutyl, 3-methylbut-2-yl, 2-methylbut-2-yl, neopentyl. Particularly preferably, $R^1$ and $R^3$ are in each case ethenyl or 2-propenyl and $R^2$ is methyl, ethyl, n-propyl, isopropyl, n-butyl, isobutyl, sec-butyl or tert-butyl. Preferably, $R^1$ and $R^3$ are identical in this embodiment.

The reaction of the aluminum alkoxide of the general formula (Ia) with the carboxylic ester of the general formula (IIIa) preferably takes place at a temperature of 20 to 200° C., preferably 60 to 180° C., particularly preferably 80 to 140° C., most preferably 100 to 130° C.

The reaction of the aluminum alkoxide of the general formula (Ia) with the carboxylic ester of the general formula (IIIa) preferably takes place at a pressure of 10 mbar to 10 bar, preferably 20 mbar to 5 bar, particularly preferably 50 mbar to 1 bar, most preferably 70 mbar to 500 mbar.

In the ligand exchange carried out in step a), an ester of the general formula $R^3\text{—CO—OCH}_2\text{—}R^2$ is formed. This ester is preferably removed from the reaction mixture before the aluminum alkoxide of the general formula (I) is used to convert the aldehyde of the general formula (II). The ester of the formula $R^3\text{—CO—OCH}_2\text{—}R^2$ may for example be separated from the reaction mixture by distillation. In one embodiment, therefore, the reaction in step a) takes place in the bottom of a distillation column, with the ester of the formula $R^3\text{—CO—OCH}_2\text{—}R^2$ being continuously removed from the reaction mixture by distillation. The temperature in the bottom of the distillation column is in this case preferably set to the reaction temperature mentioned above. The pressure preferably corresponds to the reaction pressure mentioned above. The bottoms product resulting here can be used without further purification in step b).

The reaction temperature during the reaction of the aldehyde to give the carboxylic ester is preferably below the boiling point of the aldehyde and of the carboxylic ester.

In one embodiment, the reaction of the aldehyde to give the carboxylic ester takes place at a temperature of 0 to 100° C., preferably 10 to 80° C., particularly preferably 15 to 50° C., most preferably 20 to 30° C.

Steps a) and b) may be carried out in the presence of a solvent. Preferably, however, no additional solvent is used.

If a solvent is used, consideration can be given here for example to hydrocarbons such as n-pentane, n-hexane, cyclohexane, heptane, octane, decane etc., aromatic compounds such as benzene, toluene, xylene etc., esters such as ethyl acetate, ethers such as diethyl ether, methyl tert-butyl ether etc.

EXAMPLES

Example 1 (In Situ Synthesis of the Catalyst and Subsequent Methallyl Methacrylate Synthesis)

Methacrolein (MAL) (1007 g) was cooled to −25° C. while stirring in a 2 l 3-neck round-bottomed flask under an $N_2$ atmosphere. $LiAlH_4$ (10.86 g, 2 mol % based on the amount of MAL) was added carefully in portions within 1 h 15 min so that the temperature in the flask did not exceed −20° C. After stirring for a further 15 min at −20° C., $AlCl_3$ (12.78 g, 0.67 mol % based on the amount of MAL) was added in portions (10 min) so that the temperature did not exceed −15° C. The reaction mixture was heated to 20° C. (approx. 30 min) and stirred for a further 65 h at 20° C. The conversion of MAL was 85%. The product was distilled under reduced pressure (50 mbar, boiling point of product: 79° C.). 716 g of methallyl methacrylate (MAMA) was obtained (78% yield based on free MAL not bound in the formed catalyst, purity 99.8%).

Example 2 (Preparation of the Catalyst by Ligand Exchange)

93.0 g of freshly distilled Al(Oi-Pr)$_3$ were mixed with 70 mg of TEMPOL (4-hydroxy-2,2,6,6-tetramethylpiperidin-1-oxyl), 70 mg of HQME (hydroquinone monomethyl ether) and 300 g of MAMA and distilled within 3 h using a distillation column with introduction of air. The distillation started at a bottom temperature of 118° C. and a pressure of 400 mbar. The pressure was slowly reduced within three hours to 70 mbar, so that a steady but slow condensation was apparent at the condenser. The top temperature reached values of at most 108° C. here. Initially the isopropyl methacrylate produced and then the excess MAMA were distilled off via the distillation. The end of distillation was apparent from the rise of the bottom temperature from 115° C. to 133° C., reduced boiling and reduction of the top temperature. An orange, clear and viscous bottoms product (119 g) and a clear, colorless distillate (232 g) were obtained. The bottoms product was used without further purification as catalyst for methallyl methacrylate synthesis (with the assumption of 3.81 mmol of [Al] to 1 g of this bottoms product). GC analysis of the distillate gave 31.3% by weight of methallyl methacrylate and 68.7% by weight of isopropyl methacrylate, corresponding to the degree of ligand exchange of approx. 91%.

Example 3 (Comparison with Preformed Aluminum Alkoxide Catalysts)

Methacrolein was reacted to give methallyl methacrylate with in the presence of an aluminum alkoxide prepared by ligand exchange as per example 2. In this case the reaction time and temperature in the second reaction step (conversion of MAL to MAMA) were set in accordance with the following table (test Nos 1-9).

In comparative tests preformed, commercially available aluminum alkoxides (2 mol % Al based on MAL) were mixed with 20 g of MAL (contains <0.1% dimeric methacrolein DiMAL) and 0.05 g of TEMPOL and stirred at the temperature specified in the table for the time indicated there (test Nos 10-12).

Product specimens were analyzed after hydrolysis by GC. The product parameters ascertained are given in the following table.

| No. | Catalyst | T [° C.] | Time [h] | MAL conversion [%] | MAMA yield [%] | MAMA selectivity [%] |
|---|---|---|---|---|---|---|
| 1 | see example 2 | 23 | 24 | 36.3 | 32.7 | 90.1 |
| 2 | see example 2 | 23 | 48 | 60.1 | 53.5 | 89.0 |
| 3 | see example 2 | 23 | 72 | 76.6 | 65.4 | 85.4 |
| 4 | see example 2 | 30 | 24 | 38.7 | 29.5 | 76.2 |
| 5 | see example 2 | 30 | 48 | 66.7 | 42.5 | 63.7 |
| 6 | see example 2 | 50 | 24 | 77.1 | 53.2 | 69.0 |
| 7 | see example 2 | 50 | 48 | 93.9 | 58 | 61.8 |
| 8 | see example 2 | 80 | 4 | 53.5 | 35.3 | 66.0 |
| 9 | see example 2 | 80 | 24 | 89.6 | 42.1 | 47.0 |
| 10 | Al(OiPr)$_3$ | 23 | 24 | 23.9 | 16.5 | 69.0 |
| 11 | Al(OiPr)$_3$ | 23 | 48 | 41.3 | 25.7 | 62.2 |
| 12 | Al(OnBu)$_3$ | 23 | 72 | 93.4 | 72.7 | 77.8 |

It is found that using the catalyst from Example 2, prepared by ligand exchange, allows the attainment of yields, with higher selectivity at all times, that are at least just as high as with the preformed commercially available catalysts. The yield can moreover be increased by increasing the temperature.

The invention claimed is:
1. A process for preparing a carboxylic ester, comprising:
a) preparing an aluminum alkoxide of general formula (I):

$$Al(OCH_2R^1)_3 \qquad (I),$$

by reacting an aldehyde of general formula (II):

$$R^1CHO \qquad (II),$$

with an aluminum hydride; and
b) reacting an aldehyde of general formula (II) in the presence of the aluminum alkoxide of the general formula (I) to give a carboxylic ester of general formula (III):

$$R^1-CO-OCH_2-R^1 \qquad (III);$$

wherein $R^1$ is an alkyl, alkenyl or alkynyl group.
2. The process of claim 1, wherein the reaction of the aldehyde of general formula (II) with the aluminum hydride takes place at a temperature of 70° C. to −30° C.
3. The process of claim 1, wherein $R^1$ is a —(C$_1$-C$_{12}$)-alkyl group or a —(C$_2$-C$_{12}$)-alkenyl group and may optionally be substituted by one or more substituents selected from the group consisting of:
—(C$_1$-C$_{12}$)-alkyl, —(C$_3$-C$_{12}$)-cycloalkyl, —(C$_4$-C$_{12}$)-heterocycloalkyl, —(C$_6$-C$_{20}$)-aryl, —(C$_4$-C$_{20}$)-heteroaryl, —O—(C$_1$-C$_{12}$)-alkyl, —O—(C$_3$-C$_{12}$)-cycloalkyl, —S—(C$_1$-C$_{12}$)-alkyl, —S—(C$_3$-C$_{12}$)-cycloalkyl, —COO—(C$_1$-C$_{12}$)-alkyl, —COO—(C$_3$-C$_{12}$)-cycloalkyl, —CONH—(C$_1$-C$_{12}$)-alkyl, —CONH—(C$_3$-C$_{12}$)-cycloalkyl, —N—[(C$_1$-C$_{12}$)-alkyl]$_2$, —OH, —NH$_2$, and halogen.
4. The process of claim 3, wherein $R^1$ is ethenyl or 2-propenyl.
5. The process of claim 1, wherein the aluminum hydride is a compound of empirical formula AlH$_3$ or a complex metal aluminum hydride.
6. The process of claim 5, wherein the complex metal aluminum hydride is selected from the group consisting of: LiAlH$_4$; NaAlH$_4$; KAlH$_4$; Mg(AlH$_4$)$_2$; Ca(AlH$_4$)$_2$; Ba(AlH$_4$)$_2$; Sn(II)(AlH$_4$)$_2$; Ti(IV)(AlH$_4$)$_4$; and mixtures thereof.
7. The process of claim 6, wherein an aluminum halide selected from the group consisting of AlF$_3$, AlCl$_3$, AlBr$_3$ or AlI$_3$ is added to the reaction mixture in step a).
8. The process of claim 3, wherein the aluminum hydride is a compound of empirical formula AlH$_3$ or a complex metal aluminum hydride.
9. The process of claim 8, wherein the complex metal aluminum hydride is selected from the group consisting of:

LiAlH$_4$; NaAlH$_4$; KAlH$_4$; Mg(AlH$_4$)$_2$; Ca(AlH$_4$)$_2$; Ba(AlH$_4$)$_2$; Sn(II)(AlH$_4$)$_2$; Ti(IV)(AlH$_4$)$_4$; and mixtures thereof.

10. The process of claim 2, wherein R$^1$ is a —(C$_1$-C$_{12}$)-alkyl group or a —(C$_2$-C$_{12}$)-alkenyl group and R$^1$ may optionally be substituted by one or more substituents selected from the group consisting of:

—(C$_1$-C$_{12}$)-alkyl, —(C$_3$-C$_{12}$)-cycloalkyl, —(C$_4$-C$_{12}$)-heterocycloalkyl, —(C$_6$-C$_{20}$-aryl, —(C$_4$-C$_{20}$)-heteroaryl, —O—(C$_1$-C$_{12}$)-alkyl, —O—(C$_3$-C$_{12}$)-cycloalkyl, —S—(C$_1$-C$_{12}$)-alkyl, —S—(C$_3$-C$_{12}$)-cycloalkyl, —COO—(C$_1$-C$_{12}$)-alkyl, —COO—(C$_3$-C$_{12}$)-cycloalkyl, —CONH—(C$_1$-C$_{12}$)-alkyl, —CONH—(C$_3$-C$_{12}$)-cycloalkyl, —N—[(C$_1$-C$_{12}$)-alkyl]$_2$, —OH, —NH$_2$, and halogen.

11. The process of claim 10, wherein R$^1$ is ethenyl or 2-propenyl.

12. The process of claim 11, wherein the aluminum hydride is a compound of empirical formula AlH$_3$ or a complex metal aluminum hydride.

13. The process of claim 12, wherein the complex metal aluminum hydride is selected from the group consisting of: LiAlH$_4$; NaAlH$_4$; KAlH$_4$; Mg(AlH$_4$)$_2$; Ca(AlH$_4$)$_2$; Ba(AlH$_4$)$_2$; Sn(II)(AlH$_4$)$_2$; Ti(IV)(AlH$_4$)$_4$; and mixtures thereof.

14. The process of claim 13, wherein an aluminum halide selected from the group consisting of AlF$_3$, AlCl$_3$, AlBr$_3$ or AlI$_3$ is added to the reaction mixture in step a).

\* \* \* \* \*